US008268557B2

(12) United States Patent
Valberg et al.

(10) Patent No.: US 8,268,557 B2
(45) Date of Patent: *Sep. 18, 2012

(54) METHOD OF DETECTING EQUINE POLYSACCHARIDE STORAGE MYOPATHY

(76) Inventors: Stephanie J. Valberg, Lino Lakes, MN (US); Molly E. McCue, Roseville, MN (US); James R. Mickelson, Roseville, MN (US)

( * ) Notice: Subject to any disclaimer, the term of this patent is extended or adjusted under 35 U.S.C. 154(b) by 187 days.

This patent is subject to a terminal disclaimer.

(21) Appl. No.: 12/527,117

(22) PCT Filed: Feb. 14, 2007

(86) PCT No.: PCT/US2007/062134
§ 371 (c)(1),
(2), (4) Date: Aug. 13, 2009

(87) PCT Pub. No.: WO2008/100313
PCT Pub. Date: Aug. 21, 2008

(65) Prior Publication Data
US 2010/0279286 A1 Nov. 4, 2010

(51) Int. Cl.
C07H 21/04 (2006.01)
C12Q 1/68 (2006.01)
(52) U.S. Cl. ...... 435/6.1; 435/6.11; 435/91.1; 435/91.2; 435/6.12; 536/23.1; 536/24.3
(58) Field of Classification Search .................. None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 2009/0258360 | A1 | 10/2009 | Valberg et al. |

OTHER PUBLICATIONS

Lucentini (The Scientist; 2004, vol. 24, p. 20).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Annandale et al. (Neuromuscular Disorders, vol. 14, pp. 666-674, 2004).*
McCue (Genomics, vol. 91, pp. 458-466, 2008).*
Annandale et al. AJVR, vol. 66, No. 5, pp. 839-845, May 2005).*
Dranchak et al. (AJVR, vol. 68, No. 10, pp. 1079-1084, 2007).*
Park et al. (Cytogenet Genome Res, vol. 102, pp. 211-216, 2003).*
Anderson et al., "Hyperactive glycogen synthase mutants of *Saccharomyces cerevisiae* suppress the *glc7-1* protein phosphatase mutant, *J. Bact.*, 183, 821-829 (2001).
Annandale et al., "Insulin sensitivity and skeletal muscle glucose transport in horses with equine polysaccharide storage myopathy," *Neuromuscular Disorders*, 14, 666-674 (2004).

Annandale et al., "Effects of submaximal exercise on adenine nucleotide concentrations in skeletal muscle fibers of horses with polysaccharide storage myopathy," Am J. Vet. Res., 66(5), 839-845 (2005).
Barrett et al., "Haploview: analysis and visualization of LD and haplotype maps," *Bioinformatics*, 21(2), 263-265 (2005).
Brinkmeyer-Langford et al., "A high-resolution physical map of equine homologs of HSA19 shows divergent evolution compared with other mammals," *Mamm. Genome*, 16(8), 631-649 and 5 supplemental pages (2005).
Buschiazzo et al., "Crystal structure of glycogen synthase: homologous enzymes catalyze glycogen synthesis and degradation," *EMBO Journal*, 23, 3196-3205 (2004).
Chapman N.H. & E.M. Wijsman, "Genome screens using linkage disequilibrium tests: optimal marker characteristics and feasibility," *Am. J. Hum. Genet.*, 63, 1872-1885 (1998).
Cid et al., "Identification of two essential glutamic acid residues in glycogen synthase," *J. Biol. Chem.*, 275, 33614-33621 (2000).
De La Corte et al., "Developmental Onset of Polysaccharide Storage Myopathy in 4 Quarter Horse Foals," *J. Vet. Intern. Med.*, 16, 581-587 (2002).
De La Corte et al., "Glucose uptake in horses with polysaccharide storage myopathy," *Am. J. Vet. Res.*, 60, 458-462 (1999).
De La Corte et al., "Blood glucose clearance after feeding and exercise in polysaccharide storage myopathy," *Eq. Vet. J. Suppl.*, 30, 324-328 (1999).
Dimauro et al., "Nonlysosmal Glycogenoses," In: A.G. Engel & C. Franzini-Armstrong (Eds.), *Myology*, McGraw-Hill, New York, 2004, pp. 1535-1558.
Dimauro et al., "Biochemistry and molecular genetics of human glycogenoses: an overview," *Muscle and Nerve*, Suppl. 3, S10-S17 (1995).
Dranchak, et al., "Biochemical and genetic evaluation of the role of AMP-activated protein kinase in polysaccharide storage myopathy in Quarter Horses," *Am. J. Vet. Res.*, 68 1079-1084 (2007).
Firshman et al., "Prevalences and clinical signs of polysaccharide storage myopathy and shivers in Belgian Draft Horses," *J. Am. Vet. Med. Assoc.*, 227(12), 1958-1964 (2005).
Firshman et al., "Comparison of histopathologic criteria and skeletal muscle fixation techniques for the diagnosis of polysaccharide storage myopathy in horses," *Vet. Pathol.*, 43, 257-269 (2006).
Firshman et al. "Epidemiologic characteristics and management of polysaccharide storage myopathy in Quarter Horses," *Am J Vet Res.*, 64, 1319-1327 (2003).
Furukawa et al., "Identification of $Lys^{277}$ at the active site of *Escherichia coli* glycogen synthase," *J. Biol. Chem.*, 269, 868-871 (1994).
Furukawa et al., "Role of conserved Lys-X-Gly-Gly sequence at the ADP-glucose-binding stie in *Escherichia coli* glycogen synthase," *J. Biol. Chem.*, 268, 23837-23842 (1993).
Furukawa et al., "Identification of Lysine 15 at the active site of *Escherichia coli* glycogen synthase," *J. Biol. Chem*, 265, 2086-2090 (1990).
Hanashiro et al., "Mutations of muscle glycogen synthase that disable activation by glucose 6-phosphate," *Arch. Biochem. Biophys.*, 397, 286-292 (2002).
Heutink, P. and B.A. Oostra, "Gene finding in genetically isolated populations," *Hum. Mol. Genet. 11*, 2507-2515 (2002).

(Continued)

Primary Examiner — Jeanine A Goldberg
(74) Attorney, Agent, or Firm — Viksnins Harris & Pasys PLLP

(57) ABSTRACT

The present invention relates to diagnosing Polysaccharide Storage Myopathy (PSSM) disease in equines.

11 Claims, 3 Drawing Sheets

OTHER PUBLICATIONS

Kollberg et al., "Cardiomyopathy and exercise intolerance in muscle glycogen storage disease 0," *New England J. Med.*, 357, 1507-1514 (2007).

Manchester et al., "Increased glycogen accumulation in transgenic mice overexpressing glycogen synthase in skeletal muscle," *PNAS USA*, 93, 10707-10711 (1996).

Mahrenholz et al., "Catalytic site of rabbit glycogen synthase isozymes," *J. Biol. Chem.*, 263, 10561-10567 (1988).

McCue et al., "Identification of a PSSM locus in quarter horses by whole genome association," *Plant and Animal Genomes XV Conference*, Town & Country Convention Center, San Diego, CA, Jan. 13-17, 2007, p. 595: Equine.

McCue et al., "Prevalence of polysaccharide storage myopathy in horses with neuromuscular disorders," *Eq Vet J Suppl.*, 36, 340-344 (2006).

McCue et al., "Estimated prevalence of polysaccharide storage myopathy among overtly healthy Quarter Horses in the United States", *JAVMA.*, 231, 746-750 (2007).

McCue et al., "Glycogen synthase (GYS1) mutation causes a novel skeletal muscle glycogenosis", *Genomics*, 91(5), 458-466 and 13 pages of supplemental materials (2008).

McCue et al., "The prevalence of polysaccharide storage myopathy in the Quarter Horse Population", Research Abstract Program of the 24$^{th}$ Annual ACVIM Forum Louisville, KY, May 31-Jun. 3, 2006, *J. Vet. Intern. Med.*, 20(3), 743, abstract #119, (2006).

McCue, M.E., et al., "Glycogen synthase 1 (GYS1) mutation in diverse breeds with polysaccharide storage myopathy", *Journal of Veterinary Internal Medicine*, 22(5), 1228-1233 (2008).

McDiarmid, A., "Possible familial basis to equine polysaccharide storage myopathy," *Vet. Rec.*, 156(3), 95-96 (2005).

Nielsen et al., "Sequence-selective recognition of DNA by strand displacement with a thymine-substituted polyamide," *Science*, 254, 1497-1500 (1991).

Ott, "Nonparametric Methods," *Analysis of Human Genetic Linkage*, The John Hopkins University Press, Baltimore, 272-296 (1999).

Patent Cooperation Treaty, International Search Report and Written Opinion of the International Search Authority, PCT/US2007/062134, Feb. 6, 2008, 9 pages.

Pederson, et al., "Glycogen synthase sensitivity to glucose-6-P is important for controlling glycogen accumulation in *Saccharomyces cerevisiaen*\*", *J. Biol. Chem.*, 279, 13764-13768 (2004) and Additions and Corrections, 280, 13203-13204 (2005).

Pederson et al., "Mice with elevated muscle glycogen stores do not have improved exercise performance," *Biochem. Biophys. Res. Comm.*, 331, 491-496 (2005).

Pederson et al., "Regulation of glycogen synthase: identification of residues involved in regulation by the allosteric ligand glucose-6-P and by phosphorylation," *J. Biol. Chem.*, 275, 27753-27761 (2000).

Purcell et al., "Genetic Power Calculator: design of linkage and association genetic mapping studies of complex traits," *Bioinformatics 19*, 149-150 (2003).

Raben et al., "Surprises of genetic engineering: a possible model of polyglucosan body disease," *Neurology*, 56, 1739-1745 (2001).

Rannala et al., "Joint Bayesian Estimation of Mutation Location and Age Using Linkage Disequilibrium," *Pacific Symposium on Biocomputing*, 8, 526-534 (2003).

Ribeiro, W.P. et al., "The effect of varying dietary starch and fat content on serum creatine kinase activity and substrate availability in equine polysaccharide storage myopathy," *J. Vet. Intern. Med.*, 18, 887-894 (2004).

Roach, P.J., "Glycogen and its Metabolism," *Current Molecular Med.* 2, 101-120 (2002).

Scheet et al., "A fast and flexible statistical model for large-scale population genotype data: applications to inferring missing genotypes and haplotypic phase," *Am. J. Hum. Genet.* 78, 629-644 (2006).

Skurat A.V. et al., "Rate-determining steps in the biosynthesis of glycogen in COS cells," *Arch. Biochem. and Biophys.*, 328(2), 283-288 (1996).

Skurat A.V. et al., "Rabbit skeletal muscle glycogen synthase expressed in COS cells: identification of regulatory phosphorylation sites", *J. Biol. Chem.*, 269, 25534-25542 (1994).

Tagaya et al., "A new affinity labeling reagent for the active site of glycogen synthase: uridine diphosphopyridoxal," *J. Biol. Chem.*, 260, 6670-6676 (1985).

Thomas et al, "A rapid filter paper assay for UDPglucose-glycogen glucosyltransferase, including an improved biosynthesis of UDP-$^{14}$C-glucose," *Analytical Biochemistry*, 25, 486-499 (1968).

Valberg et al., "Skeletal muscle metabolic response to exercise in horses with "tying-up" due to polysaccharide storage myopathy," *Equine Veterinary Journal*, 31(1), 43-47 (1999).

Valberg et al., "Exertional rhabdomyolysis in Quarter Horses and Thoroughbreds: one syndrome, multiple aetiologies," *Eq. Vet J. Suppl.*, 30, 533-538 (1999).

Valberg et al., "Skeletal muscle glycolytic capacity and phosphofructokinase regulation in horses with polysaccharide storage myopathy," *Am. J. Vet. Res.*, 59, 782-785 (1998).

Valberg et al., "Familial basis of exertional rhabdomyolysis in Quarter Horse-related breeds," *Am. J. Vet. Res.*, 57(3), 286-290, (1996).

Valberg et al., "Polysaccharide storage myopathy associated with recurrent exertional rhabdomyolysis in horses", *Neuromusc. Disord.*, 2(5/6), 351-359 (1992).

Valentine et al., "Incidence of polysaccharide storage myopathy in draft horse-related breeds: a necropsy study of 37 horses and a mule", *J. Vet. Diagn. Invest.*, 13, 63-68 (2001).

Valentine et al., "Polysaccharide storage myopathy in Morgan, Arabian, and Stardardbred related horses and Welsh-cross ponies", *Vet. Pathol.*, 37, 193-196 (2000).

Valentine et al., "Incidence of polysaccharide storage myopathy: necropsy study of 225 horses," *Vet. Pathol.*, 42, 823-827 (2005).

Ward, T.L., et al., "Glycogen branching enzyme (GBE1) mutation causing equine glycogen storage disease IV", *Mammalian Genome*, 15, 570-577 (2004).

Yep et al., "The active site of the *Escherichia coli* glycogen synthase is similar to the active site of retaining GT-B glycosyltransferases," *Biochem. and Biophys. Res. Comm.*, 316, 960-966 (2004).

Yep et al., "Identification and characterization of a critical region in the glycogen synthase from *Escherichia coli*," *J. Biol. Chem.*, 279, 8359-8367 (2004).

Yep et al., "The ADP-glucose binding site of the *Escherichia coli* glycogen synthase," *Arch. Biochem. and Biophys.*, 453, 188-196 (2006).

\* cited by examiner

Figure 1.

```
1     ATGCCTCTAA ACCGCACTTT GTCCATGTCC TCACTGCCAG GACTGGACGA
51    TTGGGAGGAT GAATTCGACC TGGAGAATAC AGTGCTCTTC GAGGTGGCCT
101   GGGAGGTGGC CAACAAGGTG GGTGGCATCT ACACGGTGCT ACAGACGAAG
151   GCGAAGGTGA CAGGGGATGA ATGGGCGAC AACTACTACC TGGTGGGACC
201   ATACACGGAG CAAGGCGTGA GGACCCAGGT GGAGCTGCTC GAGCCCCCAA
251   CCCCGGCCCT GAAGAGGACG CTGGACTCCA TGAACAGCAA GGGCTGCAAG
301   GTGTATTTCG GCGCTGGCT GATCGAGGGG GGCCCCCTGG TGGTGCTCCT
351   GGATGTGGGG GCCTCAGCCT GGGCCCTGGA ACGCTGGAAG GGAGAGCTTT
401   GGGACACCTG CAACATCGGG GTGCCCTGGT ACGACCGTGA GGCCAACGAC
451   GCCGTCCTTT TTGGCTTCCT CACCACCTGG TTCCTGGGTG AGTTCCTGGC
501   CCAGAGCGAG GAGAAGCCAC ATGTGGTTGC ACACTTCCAC GAGTGGTTGG
551   CGGGCATCGG GCTCTGCCTG TGCCGTGCCC GGCGGCTGCC TGTGGCTACA
601   ATCTTCACCA CCCACGCCAC GCTGCTGGGG CGATACCTGT GTGCCGGTGC
651   TGTGGACTTC TACAACAACC TGGAGAATTT CAACGTGGAC AAGGAAGCTG
701   GTGAGAGGCA AATTTATCAC CGTTACTGCA TGGAGCGGGC GGCAGCCCAC
751   TGCACTCACG TCTTCACTAC CGTGTCCCAG ATCACCGCCA TTGAGGCTCA
801   GCACCTACTC AAGAGGAAAC CAGATATCGT GACCCCCAAT GGACTGAATG
851   TGAAGAAGTT CTCTGCCATG CATGAGTTCC AGAACCTCCA TGCTCAGAGC
901   AAGGCCCGAA TCCAGGAGTT TGTGCGTGGC CATTTTTATG GGCACCTGGA
951   CTTCAACTTG GATAAGACCC TGTATTTCTT TATCGCCGGC CGCTACGAGT
1001  TCTCCAACAA GGGGCTGAC GTCTTCCTGG AGGCCTTGGC CCGGCTCAAC
1051  TATCTGCTCA GAGTAAATGG CAGCGAGCAG ACGGTGGTCG CCTTCTTCAT
1101  CATGCCGGCT CGGACCAACA ACTTCAACGT GGAAACCCTC AAGGGGCAAG
1151  CCGTGCGCAA GCAGCTCTGG GATACGGCGA ACACAGTGAA GGAGAAGTTC
1201  GGGAGGAAGC TTTACGAATC CTGCTGGTT GGGAGCCTCC CGGACATGAA
1251  CAAGATGCTG GACAAGGAGG ATTTCACTAT GATGAAGAGA GCCATCTTTG
1301  CCACGCAGCG GCAGTCTTTT CCCCTGTGT GCACCCACAA TATGCTGGAC
1351  GACTCCTCGG ACCCTATCCT GACCACCATC CGTCGAATCG GCCTCTTCAA
1401  TAGTAGTGCT GACAGGGTCA AGGTGATTTT CCACCCAGAG TTCCTCTCCT
1451  CCACGAGCCC CCTGCTCCCC GTGGACTATG AGGAGTTTGT CCGTGGCTGC
1501  CACCTTGGGG TTTTCCCCTC CTACTATGAG CCTTGGGGCT ACACACCAGC
1551  TGAGTGCACG GTTATGGGCA TCCCCAGTAT CTCCACCAAC CTCTCCGGCT
1601  TCGGCTGCTT CATGGAGGAA CACATCGCAG ACCCCTCAGC TTACGGCATC
1651  TACATTCTGG ACCGGCGGTT CCGCAGCCTG GATGATTCCT GCTCGCAGCT
1701  TACCTCCTTC CTCTACAGCT TCTGCCAGCA GAGCCGGCGG CAGCGCATCA
1751  TCCAGCGGAA CCGCACGGAG CGCCTCTCCG ACCTTCTGGA CTGGAAATAC
1801  CTAGGCCGGT ACTATATGTC CGCGCGCCAC ATGGCGCTGG CCAAGGCCTT
1851  TCCAGAACAT TTCACCTACG AGCCCGCGA GGCTGATGCG ACCCAGGGCT
1901  ACCGCTACCC ACGGCCTGCA TCGGTGCCTC CGTCGCCCTC ACTGTCACGA
1951  CACTCGAGCC CGCACCAGAG CGAGGACGAG GAGGAGCCCC GGGACGTGCC
2001  GCCCGATGAA GACAGTGAGC GCTACGACGA GGACGAGGAG GCCGCCAAGG
2051  ACCGGCGCAA CATCCGCGCC CCGGAGTGGC CGCGTCGCGC CTCCTGCACC
2101  TCTTCCACGA GCGGGAGCAA GCGCGGCTCG GTGGACACGG GGCCCTCCAG
2151  CTCGCTCAGC ACCCCAGCG AGCCCCTCAG CCCCGCCAGC TCCCTGGGCG
2201  AGGAGCGCAA CTAA (SEQ ID NO:1)
```

Figure 2.

```
                 1          11         21         31         41
Normal      TTGAAACATG GGGCCTTCTC CCCCATGCCT AGATATCGTG ACCCCCAATG
PSSM        TTGAAACATG GGGCCTTCTC CCCCATGCCT AGATATCGTG ACCCCCAATG 51         61         71         81         91
Normal      GACTGAATGT GAAGAAGTTC TCTGCCATGC ATGAGTTCCA GAACCTCCAT
PSSM        GACTGAATGT GAAGAAGTTC TCTGCCATGC ATGAGTTCCA GAACCTCCAT 101        111        121        131        141
Normal      GCTCAGAGCA AGGCCCGAAT CCAGGAGTTT GTGCGTGGCC ATTTTTATGG
PSSM        GCTCAGAGCA AGGCCCGAAT CCAGGAGTTT GTGCATGGCC ATTTTTATGG 151        161        171        181        191
Normal      GTATGTGGGC CAGATACCCA GGTCTTGAGA GAGGTGGGGG TTGGGTGCCC
PSSM        GTATGTGGGC CAGATACCCA GGTCTTGAGA GAGGTGGGGG TTGGGTGCCC 201        211        221        231
Normal      AGACTCCCGG GTCTAAGGGG GGGACAGCTA A  (SEQ ID NO:2)
PSSM        AGACTCCCGG GTCTAAGGGG GGGACAGCTA A  (SEQ ID NO:3)
```

Figure 3.

```
                       1          11         21         31
PSSM Horses       IVTPNGLNVK KFSAMHEFQN LHAQSKRRIQ EFVHGHFYG
(SEQ ID NO:4)

All other species IVTPNGLNVK KFSAMHEFQN LHAQSKRRIQ EFVRGHFYG
(SEQ ID NO:5)
```

Figure 4.

```
1    GTGGGGCATA GGAGGGGGTC CCGAGACATG AATGAGGTAG TTGACGGTCT
51   ACGCCAAGGC CCGTACCAAT TTTCTTATTG TAAAGAGCAG AGAACTACAA
101  CTCCCAGAAG ACCCTAAGTT GATGGCCTGC ATATGAGGCT GCCGGGCTGT
151  ACCCTAGAGG CTAATGGGAG GTGTAGTTTC TTTGACATTC ATTTCAGAAA
201  AGGGAAAATT ATTTTATTGG CTAAGGTGGA TATTGGTCTT CTGAAAGAGG
251  ATGGAGGTTC ACTGGATTTT GTTTTTGAGA AAAGCAGTGT TAGAACCAGT
301  TATTCTTCCC AGGCTATAGC ATCAATTCTC AATGGATGTG AGAACTACAA
351  CTCCCAGAAG GCCTCTGGCT GGCCAGCTCC TTAATATTCC TGGAATTACC
401  TTCATTTATT CATTCAACCA CATTGATCTG AATGAAGAAG TGAAACATGG
451  GACCTTCTCC CCCATGCCTA GATATCGTGA CCCCCAATGG ACTGAATGTG
501  AAGAAGTTCT CTGCCATGCA TGAGTTCCAG AACCTCCATG CTCAGAGCAA
551  GGCCCGAATC CAGGAGTTTG TGCGTGGCCA TTTTTATGGG TATGTGGGCC
601  AGATACCCAG GTCTTGAGAG AGGTGGGGGT TGGGTGCCCA GACTCCCGGG
651  TCTAAGGGAG GGGACAGCTG GGGGCTCAGA CTCTTGAGTT CCTGAGCGTC
701  AGAACAATGG CTGAGTATTG CAGGAGATCC CCGTTTAAGG AGAAAAGAGG
751  CACAAGTCCC ATGAGTCCCA TGATGCCTCT GTACTGTCTA AGATGTTCTT
801  TGCCCCTGTG GCTTCTGGGG TTTGTAGTTT TGAGCCAGGG CTAGAGGGTG
851  AGGATCTTGG CTTCACCCTG TCTTGTGGCT TTTTAG (SEQ ID NO:6)
```

Figure 5.

```
1    MPLNRTLSMS SLPGLDDWED EFDLENTVLF EVAWEVANKV GGIYTVLQTK
51   AKVTGDEWGD NYYLVGPYTE QGVRTQVELL EPPTPALKRT LDSMNSKGCK
101  VYFGRWLIEG GPLVVLLDVG ASAWALERWK GELWDTCNIG VPWYDREAND
151  AVLFGFLTTW FLGEFLAQSE EKPHVVAHFH EWLAGIGLCL CRARRLPVAT
201  IFTTHATLLG RYLCAGAVDF YNNLENFNVD KEAGERQIYH RYCMERAAAH
251  CTHVFTTVSQ ITAIEAQHLL KRKPDIVTPN GLNVKKFSAM HEFQNLHAQS
301  KARIQEFVRG HFYGHLDFNL DKTLYFFIAG RYEFSNKGAD VFLEALARLN
351  YLLRVNGSEQ TVVAFFIMPA RTNNFNVETL KGQAVRKQLW DTANTVKEKF
401  GRKLYESLLV GSLPDMNKML DKEDFTMMKR AIFATQRQSF PPVCTHNMLD
451  DSSDPILTTI RRIGLFNSSA DRVKVIFHPE FLSSTSPLLP VDYEEFVRGC
501  HLGVFPSYYE PWGYTPAECT VMGIPSISTN LSGFGCFMEE HIADPSAYGI
551  YILDRRFRSL DDSCSQLTSF LYSFCQQSRR QRIIQRNRTE RLSDLLDWKY
601  LGRYYMSARH MALAKAFPEH FTYEPREADA TQGYRYPRPA SVPPSPSLSR
651  HSSPHQSEDE EEPRDVPPDE DSERYDEDEE AAKDRRNIRA PEWPRRASCT
701  SSTSGSKRGS VDTGPSSSLS TPSEPLSPAS SLGEERN-
```

METHOD OF DETECTING EQUINE POLYSACCHARIDE STORAGE MYOPATHY

BACKGROUND OF THE INVENTION

Polysaccharide Storage Myopathy (PSSM) is a debilitating muscle disease in many and diverse breeds of horses. Previous data indicates that approximately 10% of Quarter Horses and 36% of Belgian draft horses are affected. Clinical signs vary, but can range from muscle atrophy and progressive weakness in Draft horse breeds, to acute post-exercise muscle cramping and cell damage in Quarter Horses and other breeds. All forms of PSSM in horses are highly associated with deposits of an abnormal polysaccharide in skeletal muscle fibers that are demonstrated by histochemical staining of muscle biopsies. PSSM is also characterized by as much as four times the normal level of glycogen in skeletal muscle. Mutations in genes of glucose and glycogen metabolism are known to cause various types of glycogen storage diseases (glycogenoses) in humans and animal species, of which several histologically resemble PSSM. However, none of these genes appear to be responsible for equine PSSM.

The current diagnosis of PSSM in horses is based on clinical signs of muscle cramping or progressive atrophy (depending on the breed), often with elevated serum levels of muscle enzymes, combined with the histopathology finding of abnormal polysaccharide in thin sections cut from skeletal muscle biopsies.

Muscle biopsies are invasive, require skilled veterinary personnel to collect, are relatively expensive for the owner, and take a skilled muscle histopathologist to interpret. Further, although the muscle biopsy analysis has been a highly reliable diagnostic tool, it is not now 100% specific or sensitive, and can never hope to be.

Therefore, despite the foregoing, there is a need in the art for additional diagnostic tests for diagnosing PSSM in horses.

SUMMARY OF THE INVENTION

The present invention provides a method for detecting the presence of a biomarker associated with equine Polysaccharide Storage Myopathy (PSSM). In one embodiment of the invention, the method involves obtaining a physiological sample from a horse, wherein the sample comprises nucleic acid, and determining the presence of the biomarker. As used herein, the phrase "physiological sample" is meant to refer to a biological sample obtained from a mammal that contains nucleic acid. For example, a physiological sample can be a sample collected from an individual horse, such as including, but not limited to, e.g., a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, e.g., a hair sample with roots; and/or a fluid sample, such as blood.

Examples of breeds of affected horse include, but are not limited to, Quarter Horses, Percheron Horses, Paint Horses, Draft Horses, Warmblood Horses, or other related or unrelated breeds. The phrase "related breed" is used herein to refer to breeds that are related to a breed, such as Quarter Horse, Draft Horse, or Warmblood Horse. Such breeds include, but are not limited to stock breeds such as the American Paint horse, the Appaloosa, and the Palomino. The term "Draft Horse" includes many breeds including but not limited to Clydesdale, Belgian, Percheron, and Shire horses. The term "Warmblood" is also a generic term that includes a number of different breeds. "Warmblood" simply distinguishes this type of horse from the "cold bloods" (draft horses) and the "hot bloods" (Thoroughbreds and Arabians). The method of the present invention also includes horses of crossed or mixed breeds.

The term "biomarker" is generally defined herein as a biological indicator, such as a particular molecular feature, that may affect or be related to diagnosing or predicting an individual's health. For example, in certain embodiments of the present invention, the biomarker comprises a mutant equine glycogen synthase enzyme 1 (GSY1) gene, such as a polymorphic allele of GYS1 has a substitution of G to A at nucleotide 926 in exon 6. The GYS1 gene encodes an enzyme having an R (arginine) to H (histidine) substitution at amino acid residue 309.

"Oligonucleotide probe" can refer to a nucleic acid segment, such as a primer, that is useful to amplify a sequence in the GYS1 gene that is complementary to, and hybridizes specifically to, a particular sequence in GYS1, or to a nucleic acid region that flanks GYS1.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

In one embodiment of the present invention, the method also involves contacting the sample with at least one oligonucleotide probe to form a hybridized nucleic acid and amplifying the hybridized nucleic acid. "Amplifying" utilizes methods such as the polymerase chain reaction (PCR), ligation amplification (or ligase chain reaction, LCR), strand displacement amplification, nucleic acid sequence-based amplification, and amplification methods based on the use of Q-beta replicase. These methods are well known and widely practiced in the art. Reagents and hardware for conducting PCR are commercially available. For example, in certain embodiments of the present invention, exon 6 of the equine glycogen synthase enzyme 1 gene (also referred to as GSY1), or a portion thereof, may be amplified by PCR. In another embodiment of the present invention, at least one oligonucleotide probe is immobilized on a solid surface.

The methods of the present invention can be used to detect the presence of a biomarker associated with equine Polysaccharide Storage Myopathy (PSSM) in a horse such as a foal, e.g., a neonatal foal or an aborted foal, one of a breeding pair of horses, e.g., the potential dam and/or sire, or any horse at any stage of life. The horse can be alive or dead.

Further provided by the present invention is a method for diagnosing Polysaccharide Storage Myopathy (PSSM) in a horse, the method involving obtaining a physiological sample from the horse, wherein the sample comprises nucleic acid; and detecting the presence of a biomarker in the sample, wherein the presence of the biomarker is indicative of the disease. One embodiment of the method further involves contacting the sample with at least one oligonucleotide probe to form a hybridized nucleic acid and amplifying the hybridized nucleic acid. For example, in one embodiment, exon 6 of equine glycogen synthase enzyme 1 or a portion thereof is amplified, for example, by polymerase chain reaction, strand displacement amplification, ligase chain reaction, amplification methods based on the use of Q-beta replicase and/or nucleic acid sequence-based amplification. In one embodiment of the method, the biomarker contains an equine glycogen synthase enzyme 1 gene having a G to A substitution at nucleotide 926 in exon 6 of the equine glycogen synthase enzyme 1 gene, or a gene encoding a glycogen synthase enzyme having an R to H substitution at amino acid residue 309. The method can be used to detect PSSM in a horse.

Further provided by the present invention is a kit comprising a diagnostic test for detecting the presence of equine PSSM in a horse comprising packaging material, containing, separately packaged, at least one oligonucleotide probe capable of forming a hybridized nucleic acid with GYS1 and instructions means directing the use of the probe in accord with the methods of the invention.

BRIEF DESCRIPTION OF DRAWINGS

FIG. 1. Normal Equine GYS1 Coding DNA Sequence (SEQ ID NO:1). Exon 6 is indicated in bold. The site of a G to A mutation site at nucleotide position 926 is underlined. This region of sequence is expanded below in FIG. 2.

FIG. 2. GYS1 Exon 6 and Flanking DNA Sequence from Normal (SEQ ID NO:2) and PSSM Horses (SEQ ID NO:3). Exon 6 in these equine GYS1 DNA sequences contains positions 33-150. At position 135 a G in the normal horse sequence is replaced by an A in the PSSM horse sequence. This changes the underlined three base codon from one coding for an arginine (CGT) to one coding for a histidine (CAT).

FIG. 3. Glycogen Synthase Amino Sequences Encoded by Exon 6 of the GYS1 Genes. Species included in the analysis are Human, Control Horse, Chimpanzee, Canine, Bovine, Mouse, Rat, Pig, and Zebrafish. All species have identical amino acid sequences in this region of the skeletal muscle glycogen synthase protein (SEQ ID NO:4), which represents the 39 amino acids encoded by nucleotide positions 33-150 in the DNA sequences of FIG. 2. However, PSSM horses have a histidine (H) at amino acid position 34 in this exon (underlined) (SEQ ID NO:5), while all other species have an arginine (R). This codon represents number 309 in the complete coding sequence.

FIG. 4. Horse GYS1 Intron 5, Exon 6, and Intron 6 genomic DNA sequence from which PCR primers to amplify the PSSM GYS1 mutation would be most appropriately derived (SEQ ID NO:6). Exon 6 is indicated in bold.

FIG. 5. The entire GYS 1 coding nucleotide sequence in FIG. 1 was translated to give this amino acid sequence (SEQ ID NO:9). The site of the R to H mutation at codon 309 is underlined.

DETAILED DESCRIPTION OF THE INVENTION

Horses affected with Polysaccharide Storage Myopathy (PSSM) are typically heterozygous for the affected gene.

An "allele" is a variant form of a particular gene. For example, the present invention relates, inter alia, to the discovery that some alleles of the GYS1 gene cause PSSM in horses. A "GYS1 allele" refers to a normal allele of the GYS1 locus as well as an allele carrying a variation(s) that predispose a horse to develop PSSM. The coexistence of multiple alleles at a locus is known as "genetic polymorphism." Any site at which multiple alleles exist as stable components of the population is by definition "polymorphic." An allele is defined as polymorphic if it is present at a frequency of at least 1% in the population. A "single nucleotide polymorphism (SNP)" is a DNA sequence variation that involves a change in a single nucleotide.

The terms "protein," "peptide" and "polypeptide" are used interchangeably herein.

The invention encompasses isolated or substantially purified nucleic acid compositions. In the context of the present invention, an "isolated" or "purified" DNA molecule is a DNA molecule that, by human intervention, exists apart from its native environment and is therefore not a product of nature. An isolated DNA molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention.

By "fragment" or "portion" of a sequence is meant a full length or less than full length of the nucleotide sequence encoding, or the amino acid sequence of a polypeptide or protein. As it relates to a nucleic acid molecule, sequence or segment of the invention when linked to other sequences for expression, "portion" or "fragment" means a sequence having, for example, at least 80 nucleotides, at least 150 nucleotides, or at least 400 nucleotides. If not employed for expressing, a "portion" or "fragment" means, for example, at least 9, 12, 15, or at least 20, consecutive nucleotides, e.g., probes and primers (oligonucleotides), corresponding to the nucleotide sequence of the nucleic acid molecules of the invention. Alternatively, fragments or portions of a nucleotide sequence that are useful as hybridization probes generally do not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides or more.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures used to join together DNA sequences as described, for example, in Sambrook and Russell (2001).

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, such as glycogen synthase enzyme 1, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

A "mutant" glycogen synthase enzyme 1 (GYS1) refers to the protein or fragment thereof that is encoded by a GYS1 gene having a mutation, e.g., such as might occur at the GYS1 locus. A mutation in one GYS1 allele may lead to enhanced or increased enzymatic activity in a horse heterozygous for the allele. Increased enzymatic activity can be determined by methods known to the art. Mutations in GYS1 may be-disease-causing in a horse heterozygous for the mutant GYS1 allele, e.g., a horse heterozygous for a mutation leading to a mutant gene product such as a substitution mutation in exon 6 of GYS1, such as that designated herein as G926A.

"Somatic mutations" are those that occur only in certain tissues, e.g., in liver tissue, and are not inherited in the germline. "Germline" mutations can be found in any of a body's tissues and are inherited. The present GYSE1 mutation is a germline mutation.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5°C lower than the thermal melting point ($T_m$) for the specific sequence at a defined ionic strength and pH. However, stringent conditions encompass temperatures in the range of about 1°C to about 20°C, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%; at least 80%, 81%, 82%, 83%, 84%, 85%, 86%, 87%, 88%, or 89%; or at least 90%, 91%, 92%, 93%, or 94%; or even at least 95%, 96%, 97%, 98% or 99% sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m\ 81.5° C.+16.6\ (\log M)+0.41\ (\%\ GC)-0.61\ (\% \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C.; and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. Guidance as to appropriate amino acid substitutions that do not affect biological activity of the protein of interest are well known in the art. Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally-occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms."

A "host cell" is a cell which has been transformed, or is capable of transformation, by an exogenous nucleic acid molecule. Thus, "transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will have the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified through, for example, the use of single-stranded mutagenesis. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes the non-coding sequences. For example, a DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. It may constitute an "uninterrupted coding sequence," i.e., lacking an intron, such as in a cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

The term "regulatory sequence" is art-recognized and intended to include promoters, enhancers and other expression control elements (e.g., polyadenylation signals). Such regulatory sequences are known to those skilled in the art. It should be understood that the design of the expression vector may depend on such factors as the choice of the host cell to be transfected and/or the amount of fusion protein to be expressed.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

A control element, such as a promoter, "directs the transcription" of a coding sequence in a cell when RNA polymerase binds the promoter and transcribes the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably-linked" refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" or "translation stop codon" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon. Such sequence changes can cause a mutation in the polypeptide encoded by a GYS1 gene. For example, if the mutation is a nonsense mutation, the mutation results in the generation of a premature stop codon, causing the generation of a truncated GYS polypeptide.

Nucleic Acids of the Invention

Sources of nucleotide sequences from which the present nucleic acid molecules can be obtained include any prokaryotic or eukaryotic source. For example, they can be obtained from a mammalian, such as an equine, cellular source. Alternatively, nucleic acid molecules of the present invention can be obtained from a library, such as the CHORI-241 Equine BAC library or the BAC library developed at INRA, Centre de Recherches de Jouy, Laboratoire de Génétique biochimique et de Cytogénétique, Départment de Génétique animale, 78350 Jouy-en-Josas Cedex, France.

As discussed above, the terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule that is complementary or hybridizes to a sequence in a gene of interest, i.e., a nucleic acid sequence encoding an equine glycogen synthase enzyme, and remains stably bound under stringent conditions (as defined by methods well known in the art). Thus, the RNA or DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Nucleic Acid Amplification Methods

According to the methods of the present invention, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction: The oligonucleotide probe portion is about 13 to 15 nucleotides in length in one embodiment of the invention.

Ligase chain reaction (LCR) is also carried out in accordance with known techniques. In general, the reaction is carried out with two pairs of oligonucleotide probes: one pair binds to one strand of the sequence to be detected; the other pair binds to the other strand of the sequence to be detected: Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In one embodiment of the invention, each exon of the GYS1 gene is amplified by PCR using primers based on the known sequence. The amplified exons are then sequenced using automated sequencers. In this manner, the exons of the GYS1 gene from horses suspected of having PSSM in their pedigree are sequenced until a mutation is found. Examples of such mutations include those in exon 6 of the GYS1 DNA. For example, one mutation is the G to A substitution at nucleotide base 926 in exon 6. Using this technique, additional mutations causing equine PSSM can be identified.

According to the diagnostic method of the present invention, alteration within the wild-type GYS1 locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Point mutational events may occur in regulatory regions, such as in the promoter of the gene, leading to loss or diminution of expression of the mRNA. Point mutations may also abolish proper RNA processing, leading to loss of expression of the GYS1 gene product, or to a decrease in mRNA stability or translation efficiency. PSSM is a disease caused by a point mutation at nucleic acid 926. Horses predisposed to or have PSSM only need to have one mutated allele.

Diagnostic techniques that are useful in the methods of the invention include, but are not limited to direct DNA sequencing, PFGE analysis, allele-specific oligonucleotide (ASO), dot blot analysis and denaturing gradient gel electrophoresis, and are well known to the artisan.

There are several methods that can be used to detect DNA sequence variation. Direct DNA sequencing, either manual sequencing or automated fluorescent sequencing can detect sequence variation. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA) and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result.

Detection of point mutations may be accomplished by molecular cloning of the GYS1 allele(s) and sequencing the allele(s) using techniques well known in the art. Alternatively, the gene sequences can be amplified directly from a genomic DNA preparation from equine tissue, using known techniques. The DNA sequence of the amplified sequences can then be determined.

There are six well known methods for a more complete, yet still indirect, test for confirming the presence of a mutant allele: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. For allele-specific PCR, primers are used which hybridize at their 3' ends to a particular GYS1 mutation. If the particular mutation is not present, an amplification product is not observed. Amplification Refractory Mutation System (ARMS) can also be used. Insertions and deletions of genes can also be detected by, cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as known in the art can be used.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe that is complementary to the horse wild-type GYS1 gene coding sequence. The riboprobe and either mRNA or DNA isolated from the tumor tissue are annealed (hybridized) together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the GYS1 mRNA or gene but can be a segment of either. If the riboprobe comprises only a segment of the GYS1 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR before hybridization.

Nucleic acid analysis via microchip technology is also applicable to the present invention.

DNA sequences of the GYS1 gene that have been amplified by use of PCR may also be screened using allele-specific probes. These probes are nucleic acid oligomers, each of which contains a region of the GYS1 gene sequence harboring a known mutation. For example, one oligomer may be about 30 nucleotides in length, corresponding to a portion of the GYS1 gene sequence. By use of a battery of such allele-specific probes, PCR amplification products can be screened to identify the presence of a previously identified mutation in the GYS1 gene. Hybridization of allele-specific probes with amplified GYS1 sequences can be performed, for example, on a nylon filter. Hybridization to a particular probe under stringent hybridization conditions indicates the presence of the same mutation in the tissue as in the allele-specific probe.

Alteration of GYS1 mRNA expression can be detected by any technique known in the art. These include Northern blot analysis, PCR amplification and RNase protection. Diminished mRNA expression indicates an alteration of the wild-type GYS1 gene.

Alteration of wild-type GYS1 genes can also be detected by screening for alteration of wild-type GYS1 protein, or a portion of the GYS1 protein. For example, monoclonal antibodies immunoreactive with GYS1 (or to a specific portion of the GYS1 protein) can be used to screen a tissue. Lack of cognate antigen would indicate a mutation. Antibodies specific for products of mutant alleles could also be used to detect mutant GYS1 gene product. Such immunological assays can be done in any convenient formats known in the art. These include Western blots, immunohistochemical assays and ELISA assays. Any means for detecting an altered GYS1 protein can be used to detect alteration of wild-type GYS1 genes. Functional assays, such as protein binding determinations, can be used. In addition, assays can be used that detect GYS1 biochemical function. Finding a mutant GYS1 gene product indicates alteration of a wild-type GYS1 gene.

Mutant GYS1 genes or gene products can be detected in a variety of physiological samples collected from a horse. Examples of appropriate samples include a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, especially a hair sample with roots; a fluid sample, such as blood.

The methods of diagnosis of the present invention are applicable to any equine disease in which GYS1 has a role. The diagnostic method of the present invention is useful, for example, for veterinarians, Breed Associations, or individual breeders, so they can decide upon an appropriate course of treatment, and/or to determine if an animal is a suitable candidate as a broodmare or sire.

Oligonucleotide Probes

As noted above, the method of the present invention is useful for detecting the presence of a polymorphism in equine DNA, in particular, the presence of a G to A nucleotide substitution at position 926 in exon 6 of the coding sequence of equine GYS1 (SEQ ID NO:1). This substitution results in the replacement of an arginine (R) amino acid at codon 309 by a histidine (H) in the glycogen synthase protein (SEQ ID NO:9).

Primer pairs are useful for determination of the nucleotide sequence of a particular GYS1 allele using PCR. The pairs of single-stranded DNA primers can be annealed to sequences within or surrounding the GYS1 gene in order to prime amplifying DNA synthesis of the GYS1 gene itself. A complete set of these primers allows synthesis of all of the nucleotides of the GYS1 coding sequences, i.e., the exons. The set of primers preferably allows synthesis of both intron and exon sequences. Allele-specific primers can also be used. Such primers anneal only to particular GYS1 mutant alleles, and thus will only amplify a product in the presence of the mutant allele as a template.

The first step of the process involves contacting a physiological sample obtained from a horse, which sample contains nucleic acid, with an oligonucleotide probe to form a hybridized DNA. The oligonucleotide probes that are useful in the methods of the present invention can be any probe comprised of between about 4 or 6 bases up to about 80 or 100 bases or more. In one embodiment of the present invention, the probes are between about 10 and about 20 bases.

The primers themselves can be synthesized using techniques that are well known in the art. Generally, the primers can be made using oligonucleotide synthesizing machines that are commercially available. Given the sequence of the GYS1 coding sequence as set forth in SEQ ID NO:1, design of particular primers is well within the skill of the art.

Oligonucleotide probes may be prepared having any of a wide variety of base sequences according to techniques that are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7-deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethyl guanosine, 2-methyladenosine, 2-methylguanosine, 3-methylcytidine, 5-methylcytidine, N6-methyladenosine, 7-methylguanosine, 5-methylamninomethyluridine, 5-methoxyaminomethyl-2-thiouridine, β,D-mannosylqueosine, 5-methloxycarbonylmethyluridine, 5-methoxyuridine, 2-methyltio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-Methylurdine, N-((9-beta-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in Nielsen et al., *Science,* 254, 1497-1500 (1991).

The only requirement is that the oligonucleotide probe should possess a sequence at least a portion of which is capable of binding to a known portion of the sequence of the DNA sample.

It may be desirable in some applications to contact the DNA sample with a number of oligonucleotide probes having different base sequences (e.g., where there are two or more target nucleic acids in the sample, or where a single target nucleic acid is hybridized to two or more probes in a "sandwich" assay).

The nucleic acid probes provided by the present invention are useful for a number of purposes. The probes can be used to detect PCR amplification products. They may also be used to detect mismatches with the GYS1 gene or mRNA using other techniques.

Hybridization Methodology

The DNA (or nucleic acid) sample may be contacted with the oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions that permit hybridization. Suitable conditions are well known to those skilled in the art. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

EXAMPLE 1

Method of Detecting a DNA Mutation Associated with Equine Polysaccharide Storage Myopathy The present invention relates to mutations in the GYS1 gene and their use in the diagnosis of PSSM, the diagnosis of predisposition to PSSM, and to the detection of a mutant GYS1 allele in a horse.

The present inventors discovered a mutation in the equine GYS1 gene (encoding the skeletal muscle glycogen synthase enzyme) that is present in many populations of PSSM affected horses studied to date. This was possible by first deriving the protein-encoding DNA sequence of the equine GYS1 gene from mRNA isolated from skeletal muscle of both an affected and a control horse. In both horses the sequence length from the start codon (ATG) to the stop codon (TAA) was 2,214 bases (FIG. 1) and would code for a protein of 737 amino acids. The only difference between the PSSM and control horse sequences was a G to A base substitution in exon 6 at nucleotide position 926.

The DNA sequence difference at position 926 of the GYS1 coding sequence present in skeletal muscle mRNA was subsequently confirmed in the genomic DNA of several horses. An expanded view of exon 6 with its flanking intron sequence from genomic DNA is shown in FIG. 2. FIG. 2 also shows that the change from a G to A in the DNA sequence causes the replacement of an arginine (R) amino acid at codon 309 by a histidine (H) in the glycogen synthase protein. Thus, this mutation may be referred to as the G926 to A926 DNA mutation or the R309 to H309 amino acid mutation. The normal alleles of this gene may be referred to as G926, R or R309, and the mutant alleles as A926, H or H309.

To date, no other mutations in the GYS1 gene have been shown to cause a glycogen storage disease in humans or animal species. The related GYS2 gene, encoding the liver form of glycogen synthase that is expressed in non-muscle tissues, has several known mutations that lead to a deficiency in this enzyme and fasting hypoglycemia. However, unlike the GYS2 mutations that greatly reduce the activity of the glycogen synthase enzyme and are inherited in a recessive manner, the PSSM horse muscle GYS1 mutation does not reduce the glycogen synthase activity. Rather, it appears to result in an increased glycogen synthase activity and be inherited in a dominant fashion (see Table 1 below). This region of the muscle glycogen synthase amino acid sequence contained in exon 6 is highly conserved throughout the animal kingdom, lending support to its mutation in PSSM horses being a causative mutation (FIG. 3).

The inventors have found the GYS1 R to H mutation in PSSM-affected Quarter Horses, Draft horses, and Warmbloods (Table 1), and it is likely to extend to even more breeds of horses. Approximately 80% of the Quarter Horses and Belgian Draft Horses diagnosed with PSSM by the muscle biopsy method thus far are either homozygous (have two copies of the H allele; H/H) or are heterozygous (an H and an R allele; R/H). PSSM horses with the GYS1 H allele can be of either sex, and this is consistent with; but does not prove an autosomal dominant inheritance. Only 4% of Quarter Horses and 14% of the Belgian Draft Horses with negative biopsy results were heterozygous. The inventors believe this in large part reflects the less than 100% accuracy of the current diagnostic method, but could also reflect an incomplete penetrance; i.e., carriers of the H allele may not always develop disease symptoms due to other genetic and environmental factors.

TABLE 1

GYS1 Genotype Frequencies in PSSM and Control Horses of Different Breeds

| Genotype | PSSM QH | Control QH | PSSM Belgian | Control Belgian | PSSM Warmblood | Control Warmblood |
|---|---|---|---|---|---|---|
| R/R | 18 | 85 | 4 | 29 | 1 | 4 |
| R/H | 67 | 4 | 28 | 5 | 3 | 0 |
| H/H | 4 | 0 | 4 | 0 | 0 | 0 |

That approximately 20% of the Quarter Horses and 11% of Belgians with abnormal polysaccharide in muscle biopsies and clinical signs of PSSM do not carry the GYS1 H allele is suggestive that there may be other causes of PSSM. In other words, the GYS1 mutation appears to explain most, but not all cases of equine PSSM, and there is likely to be another gene responsible for a non-GYS1 form of PSSM that will be need to be the subject of additional investigation.

The inventors have determined the GYS1 genotype frequency in random populations of horses obtained from samples submitted for the purposes of breed registration requirements. Hair root samples were taken from every 10$^{th}$ submission to ensure even distribution across the US. Table 2 indicates that the GYS1 mutation is very prevalent in four major breeds examined to date, but not yet in Thoroughbreds. The GYS1 genotype distribution in Quarter Horses and Paint Horses is similar at 6-7% heterozygous with few homozygotes for the H allele. However, approximately 42% of Percherons are heterozygous and 14% are homozygous for the H allele. Since the GYS1 H allele appears to be dominant we predict that approximately 7% of all Quarter Horses and Paint horses, 36% of all Belgians and 56% of all Percherons are actually genetically susceptible to PSSM.

TABLE 2

GYS1 Genotype Frequencies in Random Sample Populations of Different Breeds

| Genotype | Quarter Horses | Paint Horses | Belgian | Percheron | Thoroughbred |
|---|---|---|---|---|---|
| R/R | 313 (93%) | 180 (92%) | 20 (61%) | 22 (44%) | 96 (100%) |
| R/H | 21 (6%) | 14 (7%) | 13 (26%) | 21 (42%) | 0 (0%) |
| H/H | 1 (<1%) | 1 (<1%) | 5 (10%) | 7 (14%) | 0 (0%) |

The nearly complete DNA sequence of the horse GYS1 gene (Horse GYS1 Intron 5, Exon 6, and Intron 6; FIG. 4) was assembled from sequences deposited into the NCBI trace sequence archive by the Broad Institute sequencing center during their recent equine whole genome shotgun sequencing project (SEQ ID NO:6). Introns and exons of the horse GYS1 gene sequence were then predicted from the homologous GYS1 exon sequences of other mammals. Intron 5 in this sequence comprises bases 1-471. Exon 6 in this sequence is highlighted and comprises bases 472-589. Intron 6 in this sequence comprises bases 590-886. The G to A mutation in exon 6 that causes the R to H amino acid mutation at codon 309 is underlined and is at base 574.

Using the GYS1 sequence, PCR primers are developed that can amplify the PSSM GYS1 mutation. For example, a PCR primer pair that has been successfully and reliably used to amplify this region from isolated horse DNA samples lies in introns 5 and 6 and the sequence locations are also underlined (FIG. 4). These sequences are 5'-TGAAACATGGGACCT-TCTCC-3' (SEQ ID NO:7) and 5'-AGCTGTCCCCTCCCT-TAGAC-3' (SEQ ID NO:8). Many other primer pairs are also possible.

Using the above PCR primers to amplify the region, the genotype of any horse (G/G, G/A or A/A for the DNA sequence, and R/R, R/H, and H/H for the amino acid sequence) can be obtained. In this method the restriction enzyme HypCH4 V cuts the GYS1 H allele at the exon 6 site (base 574), as well as at an intronic site 100 by distant present in both the R and H alleles that serves to monitor enzyme efficiency. The products are separated by agarose gel electrophoresis and visualized by ethidium bromide staining under ultraviolet light. Many other methods of detecting the G or A nucleotide at this position of the horse GYS1 sequence are possible.

DNA testing based on the present invention now provides veterinarians and veterinary pathologists with a means to more accurately determine if a horse with clinical signs of PSSM has the heritable and most common form of disease that can be specifically attributed to this GYS1 gene mutation. All that is needed are a tissue sample containing the individual's DNA (typically hair root or blood) and appropriate PCR and sequence analysis technology to detect the G to A single nucleotide change. Such PCR primers are based in exon 6 and its flanking intron sequences as depicted in FIG. 2, sequences nearby this region depicted in FIG. 1, or in other DNA sequence from introns of this gene.

Also, DNA testing provides owners and breeders with a means to determine if any horse can be expected to produce offspring with this form of PSSM. An H/H horse would produce an affected foal 100% of the time, while an H/R horse would produce an affected foal 50% of the time when mated to an R/R horse. Mating of H/H and H/R horses would produce an affected foal 75% of the time. Breeding programs could incorporate this information in the selection of parents that could eventually reduce and even eliminate this form of PSSM in their herds.

All publications are incorporated by reference herein, as though individually incorporated by reference. The invention has been described with reference to various specific and preferred embodiments and techniques. However, it should be understood that many variations and modifications may be made while remaining within the scope of the invention.

What is claimed:

1. A method for detecting the presence of a biomarker in a horse, comprising identifying in a nucleic acid sample from the horse an adenine (A) at nucleotide 926 of SEQ ID NO:1.

2. The method of claim 1, further comprising contacting the sample with at least one oligonucleotide probe to form a hybridized nucleic acid and amplifying the hybridized nucleic acid.

3. The method of claim 2, wherein exon 6 of equine glycogen synthase enzyme 1 or a portion thereof is amplified.

4. The method of claim 2, wherein the amplification of the hybridized nucleic acid is carried out by polymerase chain reaction, strand displacement amplification, ligase chain reaction, or nucleic acid sequence-based amplification.

5. The method according to claim 2, wherein at least one oligonucleotide probe is immobilized on a solid surface.

6. A method for detecting the presence of a biomarker, comprising determining the presence of the biomarker in a physiological sample from a horse, wherein the sample comprises nucleic acid, wherein the biomarker comprises an equine GYS1 gene having an A at nucleotide 135 of SEQ ID NO:3.

7. The method of claim 6, further comprising contacting the sample with at least one oligonucleotide probe to form a hybridized nucleic acid and amplifying the hybridized nucleic acid.

8. The method of claim 7, wherein exon 6 of equine glycogen synthase enzyme 1 (GYS1) or a portion thereof is amplified.

9. The method of claim 7, wherein the amplification of the hybridized DNA is carried out by polymerase chain reaction, strand displacement amplification, ligase chain reaction, or nucleic acid sequence-based amplification.

10. The method according to claim 7, wherein at least one oligonucleotide probe is immobilized on a solid surface.

11. A method for detecting the presence of a biomarker, comprising determining the presence of the biomarker in a physiological sample from a horse, wherein the sample comprises nucleic acid, wherein the biomarker comprises a GYS1 gene that encodes an enzyme having an H at amino acid residue 309.

* * * * *

SEQUENCE LISTING

```
<160> NUMBER OF SEQ ID NOS: 9

<210> SEQ ID NO 1
<211> LENGTH: 2214
<212> TYPE: DNA
<213> ORGANISM: Equus caballus

<400> SEQUENCE: 1
atgcctctaa accgcacttt gtccatgtcc tcactgccag gactggacga ttgggaggat      60
gaattcgacc tggagaatac agtgctcttc gaggtggcct gggaggtggc caacaaggtg     120
ggtggcatct acacggtgct acagacgaag gcgaaggtga caggggatga atggggcgac     180
aactactacc tggtgggacc atacacggag caaggcgtga ggacccaggt ggagctgctc     240 gagccccaa ccccggccct gaagaggacg ctggactcca tgaacagcaa gggctgcaag     300
gtgtatttcg ggcgctggct gatcgagggg ggccccctgg tggtgctcct ggatgtgggg     360
gcctcagcct gggccctgga acgctggaag ggagagcttt gggacacctg caacatcggg     420
gtgccctggt acgaccgtga ggccaacgac gccgtccttt ttggcttcct caccacctgg     480
ttcctgggtg agttcctggc ccagagcgag gagaagccac atgtggttgc acacttccac     540
gagtggttgg cgggcatcgg gctctgcctg tgccgtgccc ggcggctgcc tgtggctaca     600
atcttcacca cccacgccac gctgctgggg cgatacctgt gtgccggtgc tgtggacttc     660
tacaacaacc tggagaattt caacgtggac aaggaagctg gtgagaggca aatttatcac     720
cgttactgca tggagcgggc ggcagcccac tgcactcacg tcttcactac cgtgtcccag     780
atcaccgcca ttgaggctca gcacctactc aagaggaaac cagatatcgt gaccccccaat    840 ggactgaatg tgaagaagtt ctctgccatg catgagttcc agaacctcca tgctcagagc     900
aaggcccgaa tccaggagtt tgtgcgtggc catttttatg ggcacctgga cttcaacttg    960
gataagaccc tgtatttctt tatcgccggc cgctacgagt tctccaacaa ggggggctgac   1020 gtcttcctgg aggccttggc ccggctcaac tatctgctca gagtaaatgg cagcgagcag   1080
acggtggtcg ccttcttcat catgccggct cggaccaaca acttcaacgt ggaaaccctc   1140 aagggcaag ccgtgcgcaa gcagctctgg gatacggcga acacagtgaa ggagaagttc   1200
gggaggaagc tttacgaatc cctgctggtt gggagcctcc cggacatgaa caagatgctg   1260
gacaaggagg atttcactat gatgaagaga gccatctttg ccacgcagcg gcagtctttt   1320
```

-continued

```
cccccccgtgt gcacccacaa tatgctggac gactcctcgg accctatcct gaccaccatc     1380
cgtcgaatcg gcctcttcaa tagtagtgct gacagggtca aggtgatttt ccacccagag     1440
ttcctctcct ccacgagccc cctgctcccc gtggactatg aggagtttgt ccgtggctgc     1500
caccttgggg ttttcccctc ctactatgag ccttggggct acacaccagc tgagtgcacg     1560
gttatgggca tccccagtat ctccaccaac ctctccggct tcggctgctt catggaggaa     1620
cacatcgcag acccctcagc ttacggcatc tacattctgg accggcggtt ccgcagcctg     1680
gatgattcct gctcgcagct tacctccttc ctctacagct tctgccagca gagccggcgg     1740
cagcgcatca tccagcggaa ccgcacggag cgcctctccg accttctgga ctggaaatac     1800
ctaggccggt actatatgtc cgcgcgccac atggcgctgg ccaaggcctt tccagaacat     1860
ttcacctacg agccccgcga ggctgatgcg acccagggcc accgctaccc acggcctgca     1920
tcggtgcctc cgtcgccctc actgtcacga cactcgagcc cgcaccagag cgaggacgag     1980
gaggagcccc gggacgtgcc gcccgatgaa gacagtgagc gctacgacga ggacgaggag     2040
gccgccaagg accggcgcaa catccgcgcc ccggagtggc cgcgtcgcgc tcctgcacc      2100 tcttccacga gcgggagcaa gcgcggctcg gtggacacgg ggccctccag ctcgctcagc     2160 accccccagcg agcccctcag ccccgccagc tccctgggcg aggagcgcaa ctaa          2214
```

<210> SEQ ID NO 2
<211> LENGTH: 231
<212> TYPE: DNA
<213> ORGANISM: Equus caballus

<400> SEQUENCE: 2

```
ttgaaacatg gggccttctc ccccatgcct agatatcgtg accccaatg gactgaatgt        60 gaagaagttc tctgccatgc atgagttcca gaacctccat gctcagagca aggcccgaat      120
ccaggagttt gtgcgtggcc attttatgg gtatgtgggc cagataccca ggtcttgaga      180
gaggtggggg ttgggtgccc agactcccgg gtctaagggg gggacagcta a                231
```

<210> SEQ ID NO 3
<211> LENGTH: 231
<212> TYPE: DNA
<213> ORGANISM: Equus caballus

<400> SEQUENCE: 3

```
ttgaaacatg gggccttctc ccccatgcct agatatcgtg accccaatg gactgaatgt        60 gaagaagttc tctgccatgc atgagttcca gaacctccat gctcagagca aggcccgaat      120
ccaggagttt gtgcatggcc attttatgg gtatgtgggc cagataccca ggtcttgaga      180
gaggtggggg ttgggtgccc agactcccgg gtctaagggg gggacagcta a                231
```

<210> SEQ ID NO 4
<211> LENGTH: 39
<212> TYPE: PRT
<213> ORGANISM: Equus caballus

<400> SEQUENCE: 4

```
Ile Val Thr Pro Asn Gly Leu Asn Val Lys Lys Phe Ser Ala Met His
 1               5                  10                  15

Glu Phe Gln Asn Leu His Ala Gln Ser Lys Arg Arg Ile Gln Glu Phe
             20                  25                  30

Val His Gly His Phe Tyr Gly
         35
```

```
<210> SEQ ID NO 5
<211> LENGTH: 39
<212> TYPE: PRT
<213> ORGANISM: Unknown
<220> FEATURE:
<223> OTHER INFORMATION: Description of Unknown Organism: Unknown GYS
      amino acid sequence from various species

<400> SEQUENCE: 5

Ile Val Thr Pro Asn Gly Leu Asn Val Lys Lys Phe Ser Ala Met His
 1               5                  10                  15

Glu Phe Gln Asn Leu His Ala Gln Ser Lys Arg Arg Ile Gln Glu Phe
            20                  25                  30

Val Arg Gly His Phe Tyr Gly
         35

<210> SEQ ID NO 6
<211> LENGTH: 886
<212> TYPE: DNA
<213> ORGANISM: Equus caballus

<400> SEQUENCE: 6
gtggggcata ggaggggtc ccgagacatg aatgaggtag ttgacggtct acgccaaggc      60
ccgtaccaat tttcttattg taaagagcag agaactacaa ctcccagaag accctaagtt    120
gatggcctgc atatgaggct gccgggctgt accctagagg ctaatgggag gtgtagtttc    180
tttgacattc atttcagaaa agggaaaatt attttattgg ctaaggtgga tattggtctt    240
ctgaaagagg atggaggttc actggatttt gtttttgaga aaagcagtgt tagaaccagt    300
tattcttccc aggctatagc atcaattctc aatggatgtg agaactacaa ctcccagaag    360
gcctctggct ggccagctcc ttaatattcc tggaattacc ttcatttatt cattcaacca    420
cattgatctg aatgaagaag tgaaacatgg gaccttctcc ccatgcctac gatatcgtga    480 ccccaatgg actgaatgtg aagaagttct ctgccatgca tgagttccag aacctccatg    540
ctcagagcaa ggcccgaatc aggagtttg tgcgtggcca ttttatggg tatgtgggcc    600 agatacccag gtcttgagag aggtgggggt tgggtgccca gactcccggg tctaagggag    660
gggacagctg ggggctcaga ctcttgagtt cctgagcgtc agaacaatgg ctgagtattg    720
caggagatcc ccgtttaagg agaaaagagg cacaagtccc atgagtccca tgatgcctct    780
gtactgtcta agatgttctt tgcccctgtg gcttctgggg tttgtagttt tgagccaggg    840
ctagagggtg aggatcttgg cttcaccctg tcttgtggct tttag                    886

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgaaacatgg gaccttctcc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```
agctgtcccc tcccttagac                                                    20

<210> SEQ ID NO 9
<211> LENGTH: 737
<212> TYPE: PRT
<213> ORGANISM: Equus caballus

<400> SEQUENCE: 9

Met Pro Leu Asn Arg Thr Leu Ser Met Ser Leu Pro Gly Leu Asp
 1               5                  10                  15

Asp Trp Glu Asp Glu Phe Asp Leu Glu Asn Thr Val Leu Phe Glu Val
            20                  25                  30

Ala Trp Glu Val Ala Asn Lys Val Gly Gly Ile Tyr Thr Val Leu Gln
            35                  40                  45

Thr Lys Ala Lys Val Thr Gly Asp Glu Trp Gly Asp Asn Tyr Tyr Leu
        50                  55                  60

Val Gly Pro Tyr Thr Glu Gln Gly Val Arg Thr Gln Val Glu Leu Leu
 65              70                  75                  80

Glu Pro Pro Thr Pro Ala Leu Lys Arg Thr Leu Asp Ser Met Asn Ser
                85                  90                  95

Lys Gly Cys Lys Val Tyr Phe Gly Arg Trp Leu Ile Glu Gly Gly Pro
            100                 105                 110

Leu Val Leu Leu Asp Val Gly Ala Ser Ala Trp Ala Leu Glu Arg
            115                 120                 125

Trp Lys Gly Glu Leu Trp Asp Thr Cys Asn Ile Gly Val Pro Trp Tyr
        130                 135                 140

Asp Arg Glu Ala Asn Asp Ala Val Leu Phe Gly Phe Leu Thr Thr Trp
145                 150                 155                 160

Phe Leu Gly Glu Phe Leu Ala Gln Ser Glu Glu Lys Pro His Val Val
                165                 170                 175

Ala His Phe His Glu Trp Leu Ala Gly Ile Gly Leu Cys Leu Cys Arg
            180                 185                 190

Ala Arg Arg Leu Pro Val Ala Thr Ile Phe Thr Thr His Ala Thr Leu
        195                 200                 205

Leu Gly Arg Tyr Leu Cys Ala Gly Ala Val Asp Phe Tyr Asn Asn Leu
    210                 215                 220

Glu Asn Phe Asn Val Asp Lys Glu Ala Gly Glu Arg Gln Ile Tyr His
225                 230                 235                 240

Arg Tyr Cys Met Glu Arg Ala Ala Ala His Cys Thr His Val Phe Thr
                245                 250                 255

Thr Val Ser Gln Ile Thr Ala Ile Glu Ala Gln His Leu Leu Lys Arg
            260                 265                 270

Lys Pro Asp Ile Val Thr Pro Asn Gly Leu Asn Val Lys Lys Phe Ser
        275                 280                 285

Ala Met His Glu Phe Gln Asn Leu His Ala Gln Ser Lys Ala Arg Ile
    290                 295                 300

Gln Glu Phe Val Arg Gly His Phe Tyr Gly His Leu Asp Phe Asn Leu
305                 310                 315                 320

Asp Lys Thr Leu Tyr Phe Phe Ile Ala Gly Arg Tyr Glu Phe Ser Asn
                325                 330                 335

Lys Gly Ala Asp Val Phe Leu Glu Ala Leu Ala Arg Leu Asn Tyr Leu
            340                 345                 350

Leu Arg Val Asn Gly Ser Glu Gln Thr Val Val Ala Phe Phe Ile Met
        355                 360                 365

```
Pro Ala Arg Thr Asn Asn Phe Asn Val Glu Thr Leu Lys Gly Gln Ala
370                 375                 380

Val Arg Lys Gln Leu Trp Asp Thr Ala Asn Thr Val Lys Glu Lys Phe
385                 390                 395                 400

Gly Arg Lys Leu Tyr Glu Ser Leu Leu Val Gly Ser Leu Pro Asp Met
                405                 410                 415

Asn Lys Met Leu Asp Lys Glu Asp Phe Thr Met Met Lys Arg Ala Ile
            420                 425                 430

Phe Ala Thr Gln Arg Gln Ser Phe Pro Pro Val Cys Thr His Asn Met
            435                 440                 445

Leu Asp Asp Ser Ser Asp Pro Ile Leu Thr Thr Ile Arg Arg Ile Gly
450                 455                 460

Leu Phe Asn Ser Ser Ala Asp Arg Val Lys Val Ile Phe His Pro Glu
465                 470                 475                 480

Phe Leu Ser Ser Thr Ser Pro Leu Leu Pro Val Asp Tyr Glu Glu Phe
                485                 490                 495

Val Arg Gly Cys His Leu Gly Val Phe Pro Ser Tyr Tyr Glu Pro Trp
            500                 505                 510

Gly Tyr Thr Pro Ala Glu Cys Thr Val Met Gly Ile Pro Ser Ile Ser
            515                 520                 525

Thr Asn Leu Ser Gly Phe Gly Cys Phe Met Glu Glu His Ile Ala Asp
530                 535                 540

Pro Ser Ala Tyr Gly Ile Tyr Ile Leu Asp Arg Arg Phe Arg Ser Leu
545                 550                 555                 560

Asp Asp Ser Cys Ser Gln Leu Thr Ser Phe Leu Tyr Ser Phe Cys Gln
                565                 570                 575

Gln Ser Arg Arg Gln Arg Ile Ile Gln Arg Asn Arg Thr Glu Arg Leu
            580                 585                 590

Ser Asp Leu Leu Asp Trp Lys Tyr Leu Gly Arg Tyr Tyr Met Ser Ala
            595                 600                 605

Arg His Met Ala Leu Ala Lys Ala Phe Pro Glu His Phe Thr Tyr Glu
610                 615                 620

Pro Arg Glu Ala Asp Ala Thr Gln Gly Tyr Arg Tyr Pro Arg Pro Ala
625                 630                 635                 640

Ser Val Pro Pro Ser Pro Ser Leu Ser Arg His Ser Ser Pro His Gln
                645                 650                 655

Ser Glu Asp Glu Glu Glu Pro Arg Asp Val Pro Pro Asp Glu Asp Ser
            660                 665                 670

Glu Arg Tyr Asp Glu Asp Glu Glu Ala Ala Lys Asp Arg Arg Asn Ile
            675                 680                 685

Arg Ala Pro Glu Trp Pro Arg Arg Ala Ser Cys Thr Ser Ser Thr Ser
690                 695                 700

Gly Ser Lys Arg Gly Ser Val Asp Thr Gly Pro Ser Ser Ser Leu Ser
705                 710                 715                 720

Thr Pro Ser Glu Pro Leu Ser Pro Ala Ser Ser Leu Gly Glu Glu Arg
                725                 730                 735

Asn
```